Figure 1:
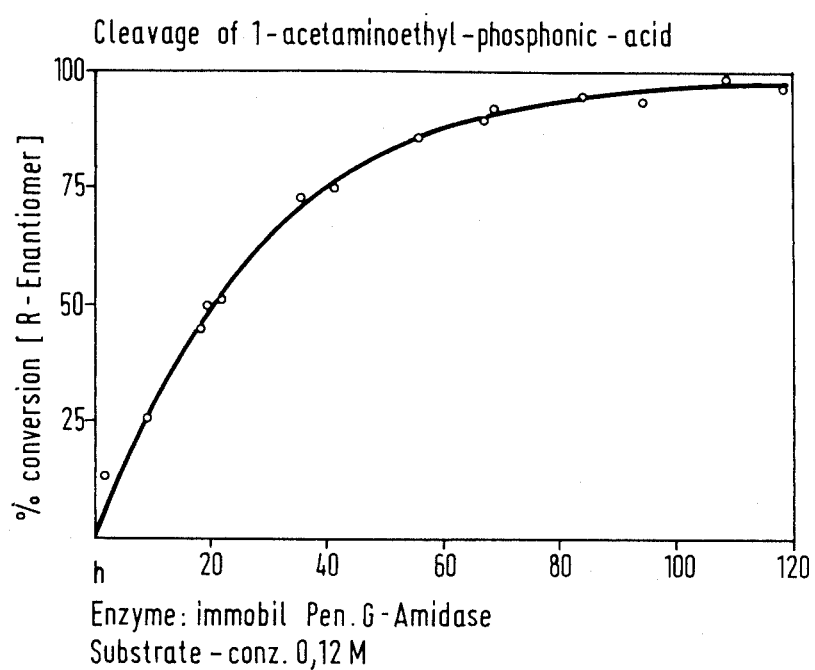

United States Patent [19]

Zimmermann et al.

[11] Patent Number: 4,859,602

[45] Date of Patent: Aug. 22, 1989

[54] PROCESS FOR THE PREPARATION OF STEREOISOMERS OF 1-AMINOALKYLPHOSPHONIC AND PHOSPHINIC ACIDS

[75] Inventors: Gerd Zimmermann, Mannheim; Josef Maier; Manfred Gloger, both of Weilheim, all of Fed. Rep. of Germany

[73] Assignee: Boehringer Mannheim GmbH, Mannheim, Fed. Rep. of Germany

[21] Appl. No.: 774,140

[22] Filed: Sep. 9, 1985

[30] Foreign Application Priority Data

Sep. 25, 1984 [DE] Fed. Rep. of Germany ....... 3435156

[51] Int. Cl.$^4$ ............................................. C12P 41/00
[52] U.S. Cl. ..................................... 435/280; 435/128; 435/129; 260/502.4 R; 562/15
[58] Field of Search ............... 435/117, 128, 129, 280; 260/502.4 R

[56] References Cited

U.S. PATENT DOCUMENTS

| | | | |
|---|---|---|---|
| 4,151,229 | 4/1979 | Zondler | 558/145 |
| 4,226,941 | 10/1980 | Goi et al. | 435/280 |
| 4,235,973 | 11/1980 | Tschang et al. | 435/180 X |
| 4,247,643 | 1/1981 | Krämer et al. | 435/180 X |
| 4,389,488 | 6/1983 | Grabley et al. | 435/280 |

FOREIGN PATENT DOCUMENTS

| | | | |
|---|---|---|---|
| 0141223 | 5/1985 | European Pat. Off. | |
| 176068 | 4/1986 | European Pat. Off. | 435/128 |
| 1369462 | 10/1974 | United Kingdom | 435/116 |

OTHER PUBLICATIONS

Otvös et al, Biochem. and Biophys. Res. Comm., vol. 44, No. 5, pp. 1056–1064 (1971).
Rossi et al, J. Org. Chem., vol. 43, No. 13 (1978), pp. 2576–2581, 2222–2225.
Romeo et al, Tetrahedron Ltrs., No. 21, pp. 1799–1802 (1971).
J. Telegdi, et al.: "Enzymatic Resoluton of Alpha-Aminophosphonic Acids", pp. 221–225, Hungarian Acad. of Sciences.
Chemical Abstracts, vol. 101, (1984), 53353c.

*Primary Examiner*—Charles F. Warren
*Assistant Examiner*—Carolyn S. Greason
*Attorney, Agent, or Firm*—Felfe & Lynch

[57] ABSTRACT

The present invention provides a process for the preparation of the stereoisomers of 1-aminoalkylphosphonic acids and of 1-aminoalkylphosphinic acids by enzymatic resolution of their racemic N-acyl derivatives and subsequent deacylation, wherein the enzymatic resolution is carried out with penicillin G amidase.

12 Claims, 2 Drawing Sheets

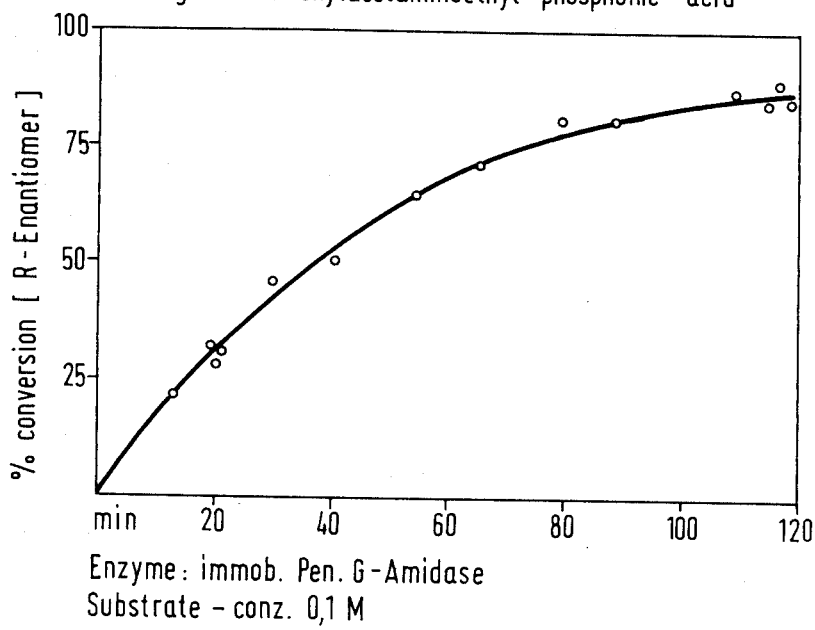

PROCESS FOR THE PREPARATION OF STEREOISOMERS OF 1-AMINOALKYLPHOSPHONIC AND PHOSPHINIC ACIDS

The present invention is concerned with a process for the preparation of stereoisomers of 1-aminoalkylphosphonic acids and of 1-aminoalkylphosphonic acids.

Peptide-like derivatives of 1-aminoalkylphosphonic acids and also of 1-aminoalkylphosphonic acids possess antibacterial effectiveness with regard to gram-positive and gram-negative micro-organisms and potentiate the activity of antibiotics, for example of penicillins, cephalosporins and D-cycloserine. In this connection, alaphosphalin, a dipeptide of L-alanine and L-aminoethylphosphonic acid, is of especial importance.

The derivatives of 1-aminoalkylphosphonic acids and of 1-aminoalkylphosphinic acids derived from the pure stereoisomeric forms and especially the derivatives derived from the L-form (R form, for the nomenclature, cf. P. Kafarski et al., Can. J. Chem., 61, 2425/1983) thereby show, in general, the greater biological activity (cf. Federal Republic of Germany Patent Specification No. 26 02 183; F. R. Atherton et al., Antimicrobial Agents and Chemotherapy, 15, May, 1979, p. 677).

The optically-active forms of the L-aminoalkylphosphonic and -phosphinic acids can be prepared by chemical racemate resolution or by asymmetrical synthesis from optically-active precursors (cf. P. Kafarski et al., Can. J. Chem., 61, 2425/1983; J. W. Huber et al., Tetrahedron Letters, 33, 3049/1979; A. Vasella and R. Veffray, Helv. Chim. Acta, 65, 1983/1982).

The resolution of racemic N-acetyl- or N-chloroacetylaminophosphonic acids into the optical antipodes with amino acid acylases has been described by J. Telegdi et al., Int. Conf. Chem. Biotechnol. Biol. Act. Nat. Prod. (Proc.), 1st Meeting, Vol. 3 (2), pp. 221–225/1981). However, for this process, large amounts of enzyme (50 to 80 mg. enzyme)/1 mmole of substrate) and long resolution times (several hours at 37°–40° C.) are necessary.

Therefore, it is an object of the present invention to provide an enzymatic process for the preparation of the stereoisomers of 1-aminoalkylphosphonic acids and of 1-aminoalkylphosphinic acids which, in a simple and economic manner (broad substrate specificity, high enzyme activity, enzyme stability and stereospecificity, high rates of resolution, good technical carrying out) leads to the isomers with a high optical purity.

This object can be achieved by carrying out the enzymatic resolution of the racemic N-acyl derivatives of 1-aminoalkylphosphonic acid and -phosphinic acids with a penicillin G-amidase (penicillin G-acylase).

Thus, we have, surprisingly, found out that, for example, the N-acetyl derivatives but also other N-acyl derivatives of 1-aminoalkylphosphonic and -phosphinic acids can be stereoselectively resolved with very high rates of resolution and high optical purity. The rates of resolution can be influenced by appropriate choice of the N-acyl radicals.

Therefore, according to the present invention, there is provided a process for the preparation of the stereoisomers of 1-aminoalkylphosphonic acids and of 1-aminoalkylphosphinic acids by enzymatic resolution of their racemic N-acyl derivatives and subsequent deacylation, wherein the enzymatic resolution is carried out with penicillin G-amidase.

From the prior art, it is admittedly known to use penicillin acrylases for the enzymatic resolution of some N-acyl derivatives, namely for the resolution of N-acyl derivatives of α-amino acids and N-phenylacetyl derivatives of primary amines and aminoalcohols (cf. D. Rossi et al., J. Org. Chem., 43, 2567/1978; D. Rossi, J. Org. Chem., 44, 2222/1979; A. Romeo et al., Tetrahedron Letters, 21, 1799/1971), for the splitting off of phenylacetyl protective groups of lysine incorporated into peptides (F. Brotnik et al., Collect. Czechoslovak. Chem. Commun., 46, 1983/1981), for the resolution of the antibiotic N-acylthienamycin (European Patent Specification No. 0000931) and for the preparation of L-phosphinothrycine (L-2-amino-4-methylphosphinobutyric acid) by resolution of the racemate (European Patent Application No. 81110474.4). However, the use of penicillin acrylases for the enzymatic resolution of N-acyl derivatives of 1-aminoalkylphosphonic and -phosphinic acids is hitherto not known.

It is, however, also known that even small changes in the aminoacid part of the substrate lead to a very considerable decrease of the enzymatic activity of penicillin G-amidase (cf. A. Plaskie et al., J. Antibiotics, 31, 783/1978); from the known use of penicillin acylase for the enzymatic resolution of N-acyl derivatives of α-aminoacids and primary amines, it was, therefore, certainly not to have been expected that N-acyl derivatives of 1-aminoalkylphosphonic and -phosphinic acids can also be resolved stereoselectively by enzymatic resolution with pencillin acylase with a high rate of reaction (rate of resolution) and high optical purity.

The process according to the present invention displays a very broad substrate specificity with regard to the N-acyl-R,S-1-aminoalkylphosphonic and -phosphinic acids. In general, the resolution activity decreases with increasing number of carbon atoms (chain length) of the 1-aminoalkylphosphonic acids and -phosphinic acids; in particular, the resolution activity and rate of resolution depend, however, upon the nature of the substituents on the 1-amino group, i.e. thus upon the nature of the acyl radical. Thus, for example, 1-acetaminoethylphosphonic acid is reacted with a specific activity of 0.5 U/g., whereas 1-phenylacetaminoethylphosphonic acid is reacted with a specific activity of 3000 U/g. Therefore, by appropriate choice of the N-acyl radical, it is possible to compensate for a decrease of the activity brought about by a higher number of carbon atoms in the aminoalkylphosphonic or -phosphinic acids.

Penicillin G-amidases used according to the present invention (penicillin G-acrylases, penicillin amidohydrolases) are enzymes which are able to split penicillin into 6-aminopenicillanic acid. They are formed by prokaryontric micro-organisms, such as especially by *Escherichia coli* (M. Cole et al., Meth. Enzym., 43, 698/1975) and are known under the EC No. 3.5.1.11. According to the present invention, penicillin G-amidase from *E. coli*, DSM 1900 (ATCC 11105) is especially preferred.

The penicillin G-amidase used according to the present invention can be employed as the free, watersoluble enzyme, for exampled as a lyophilisate, or also as immobilised enzyme in water-insoluble form.

In general, the substrate concentrations are from 0.1 mol/liter to the limit of solubility in an aqueous or aqueous-organic reaction medium. As aqueous-organic reaction medium, there can be used one which is conventional for enzyme reactions and especially one which, besides water, preferably contains an organic solvent which is readily miscible with or soluble in water, especially a lower alcohol, for example ethanol. However, an aqueous reaction medium is preferably used.

The reaction temperature is preferably from 20° to 60° C., a temperature of 37° C., being especially preferred. The period of reaction depends especially upon the enzyme activity, the enzyme and substrate concentration and the reaction temperature. As a rule, the reaction is carried out for a period of time of from 2 to 120 hours. The enzyme used according to the present invention is sufficiently active at pH values of from about 5.0 to 8.5, the optimum pH value being 7. Therefore, it is preferable to operate at pH values of from 5.5 to 8.5 and especially at pH 7. The reaction can thereby be carried out without or in the presence of an appropriate buffer, for example of a phosphate buffer. The pH values are preferably controlled with an autotitration system.

Especially for comparatively large batches on a technical scale and for economic reasons (repeated use of the enzyme, stability), it is preferable to use the enzyme in immobilised form. The reaction can then be carried out continuously in a reactor suitable for immobilised enzymes (for example a column reactor or a batch reactor; cf. for example D. H. Gräf, Pharmazie in unserer Zeit, 6, 43/1977), for example in a column process, or also discontinuously (batchwise). As immobilised enzyme, there can be used, for example, carrier-bound penicillin G-amidase (Boehringer Mannheim GmBH). Under the reaction conditions, the penicillin G-amidase is biologically and mechanically stable for several weeks and can, therefore, be used repeatedly in reactors; after 40 days (0.2 mole/liter of substrate solution: 37° C.), the loss of activity is <5%. As reactors, it is preferred to use batch reactors, for example stirrer vessel reactors, because, in the case of these reactors, an optimum pH control can easily be carried out.

The enzymatic resolution can be easily monitored analytically in known manner; the resolution of N-acetyl derivatives is preferably monitored by a discontinuous enzymatic acetate determination, whereas the resolution of other N-acyl derivatives, for example of chloroacetyl or phenylacetyl derivatives, is preferably carried out with the help of the known ninhydrin methods for the determination of free amino groups. The stereoselective resolution can be detected via a polarimetric measurement of the isolated R-1-aminophosphonic acids or via a 50% approximation of the conversion. Technical reactors can be controlled via a fine measurement of the change of speed of rotation in the reaction solution.

The working up of the reaction mixtures of the enzymatic resolution (resolution batches) can be done, for example, according to the following two methods:

1. The reaction mixture acidified with acetic acid is evaporated and the S-1-acylaminoalkylphosphonic acid and the carboxylic acid liberated by enzymatic hydrolysis of the acyl radical is extracted with ethanol. As residue, there remains the R-1-aminoalkylphosphonic acid which is insoluble in ethanol.
2. The resolution bath is chromatographed on a strongly acidic ion exchanger in the H+-form. Using water as elution agent, there are thereby successively eluted the S-1-acylaminoalkylphosponic acid, together with the carboxylic acid of the acyl residue, and subsequently the R-1-aminoalkylphosphonic acid in pure form. The carboxylic acid of the acyl residue can be separated from the S-1-acylaminoalkylphosphinic acid by simple extraction with organic solvents. As a rule, the phosphonic acid remains in the aqueous phase and can be isolated by evaporation. The N-acylated S-1-aminoalkylphosphonic acid is deacylated, for example, by boiling with 6 mol/l aqueous hydrochloric acid. The aminophosphonic acid is isolated in known manner by treatment of the solution of the hydrochloride in ethanol with propylene oxide or by chromatography on a strongly acid ion exchanger in the H+-form.

In analogous manner, there can be carried out the working up of a resolution batch of a 1-acylaminoalkylphosphinic acid.

The R- and S-isomers of the 1-aminoalkylphosphonic acids and 1-aminoalkylphosphinic acids are, by means of the process according to the present invention, obtained with a high optical purity (>95%).

The process according to the present invention is especially suitable for the preparation of stereoisomers of 1-aminoalkylphosphonic acids of the general formula:

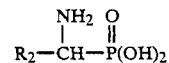

wherein $R_2$ is a branched or preferably straight-chained alkyl radical containing up to 6 and especially up to 4 carbon atoms, which can optionally also be substituted, for example, by halogen, hydroxyl, alkoxy with up to 3 carbon atoms, phenyl and/or phenoxy, or $R_2$ is a phenyl radical.

The radical $R_2$ can therefore, be, for example, methyl, hydroxymethyl, ethyl, propyl, isopropyl, butyl, isobutyl, tert.-butyl, phenyl or benzyl. For 1-aminoalkylphosphinic acids of analogous constitution, $R_2$ can have the same meaning.

In the racemic 1-acylaminoalkylphosphonic acids or -phosphinic acids used as starting materials for the enzymatic resolution according to the present invention, the acyl radical $R_1$—CO— is especially one in which $R_1$ is a branched or preferably straight-chained alkyl radical with up to 6 carbon atoms, which can possibly be substituted by halogen, hydroxy, alkoxy with up to 3 carbon atoms, phenyl, phenoxy and/or thienyl, whereby a phenyl or phenoxy radical can also be substituted, for example by alkyl with up to 3 carbon atoms, hydroxyl, nitro, amino, halogen and/or alkoxy with up to 3 carbon atoms. Therefore, the radical $R_1$ can be, for example, methyl, butyl, chloromethyl, benzyl, phenoxymethyl, 2-methylbenzyl, 4-nitrobenzyl, 4-hydroxybenzyl, 4-aminobenzyl, thienyl-(2)-, 4-chlorobenzyl or 4-methoxybenzyl.

The 1-acylaminoalkylphosphonic acids used as starting materials can be prepared by methods known from peptide chemistry by the reaction of appropriate 1-aminoalkylphosphonic acids with activated carboxylic acid derivatives or carboxylic acids in the presence of a condensation agent. The 1-acylaminoalkylphosphinic acids are obtainable in an analogous manner. As activated carboxylic acid derivatives, there can be used, for example, acid chlorides, symmetrical anhydrides or mixed anhydrides with carbonic acid monoalkyl esters, active esters, for example p-nitrophenyl esters, 2,4,5-trichlorophenyl esters, N-hydroxysuccinimide or 1-N-hydroxybenzotriazole esters. As condensation agents, there are mainly used carbodiimides, for example dicyclohexylcarbodiimide and N,N'-carbonyldiimidazole.

The amino group of the zwitterionic 1-aminoalkylphosphonic acid is preferably liberated by neutralisation of the phosphonic acid group with an alkali metal base, for example sodium hydroxide, or with a tertiary amine base, for example triethylamine. However, the aminoalkylphosphonic acids can also be acylated in the form of their alkyl esters or trialkylsilyl esters with an activated carboxylic acids. After the acylation reaction, the phosphonic acid alkyl esters can be split according to known methods by reaction with hydrobromic acid in glacial acetic acid or trimethyliodo- or bromosilane or trimethylchlorosilane/sodium iodide. Trialkylsilyl esters are hydrolysed very simply by water.

Depending upon the hydrolysis stability of the reaction components, the acylation reaction can be carried out in water, in a water/alcohol mixture or in an inert organic solvent, for example methylene chloride, acetone, acetonitrile, tetrahydrofuran, dimethylformamide or the like. The same applies to the phosphinic acid derivatives.

The racemic 1-aminoalkylphosphonic acids and -phosphinic acids are known or can be prepared by known processes (cf., for example, Synthesis, 883/1977; 479/1978; Pol. J. Chem., 52, 2271/1978).

The following Examples are given for the purpose of illustrating the present invention:

1. SYNTHESIS OF THE 1-ACYLAMINOALKYLPHOSPHONIC ACIDS

Example 1

10 g. R,S-1-aminoethylphosphonic acid are dissolved in 60 ml. of water and mixed, while stirring, with 4 mol/l sodium hydroxide to pH 9. Then, while cooling with ice, 12.3 g. phenylactic acid chloride are added dropwise thereto, the pH of the reaction being maintained at 9 by the addition of 4 mol/l sodium hydroxide. The ice-bath is removed and the mixture is stirred at ambient temperature until the pH value remains at 9 without the further addition of sodium hydroxide. The alkaline phase is extracted with diethyl ether and the aqueous phase subsequently acidified with hydrochloric acid. Fine white crystals precipitate out which are filtered off with suction and dried. For purification, they are recrystallised from isobutyl methylene ketone. There are obtained 9.5 g. (49% of theory) R,S-1-phenylacetaminoethylphosphonic acid; m.p. 140°–143° C. (decomp.).

The 1-acylaminoalkylphosphonic acids set out in the following Table 1 are prepared in an analogous manner. Some of the compounds are isolated from the acidic aqueous phase by extraction with ethyl acetate or by filtration over a strongly acidic ion exchanger in the H+-form (cf. remarks in Table 1).

TABLE 1

$$R_1-CO-NH-\underset{*}{\overset{R_2}{\underset{|}{CH}}}-\overset{O}{\overset{\|}{P}}(OH)_2$$

R,S

| No. | $R_1$ | $R_2$ | m.p. in °C. (solvent) |
|---|---|---|---|
| 1.1 | 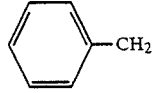 | −CH(CH₃)(CH₃) [a] | 141–143° (ethyl acetate diethyl ether) |
| 1.2 | | −CH₂−CH(CH₃)(CH₃) [a] | 125–126° (decomp.) (ethyl acetate/ ligroin) |
| 1.3 | | 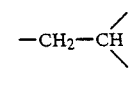 [a] | 143–146° (decomp.) (ethyl acetate/ ligroin) |
| 1.4 | | 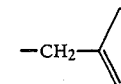 [a] | 164–167° (ethyl acetate/ diethyl ether) |
| 1.5 | | −CH₂−OH [b] | 208° (decomp.) (acetone/water) |
| 1.6 | 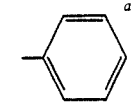 | −CH₃ | 163–168° (water) |
| 1.7 | 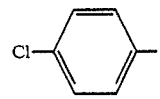 | −CH₃ | 180–182° (decomp.) |

TABLE 1-continued $$R_1-CO-NH-\underset{\underset{R,S}{*}}{\overset{R_2}{\underset{|}{CH}}}-\overset{O}{\underset{||}{P}}(OH)_2$$

| No. | $R_1$ | $R_2$ | m.p. in °C. (solvent) |
|---|---|---|---|
| 1.8 | (2-thienyl-CH$_2$—) $^b$ | —CH$_3$ | 146–150° (water) |
| 1.9 | (2-methylphenyl-CH$_2$—) | —CH$_3$ | 153–156° (1. water, 2. ethyl acetate) |
| 1.10 | CH$_3$—(CH$_2$)$_4$— $^b$ | —CH$_3$ | 92–101° (ethyl acetate) |
| 1.11 | (phenyl-O-CH$_2$—) $^a$ | —CH$_3$ | 123–125° (decomp.) (ethyl acetate/ ligroin) |
| 1.12 | Cl—CH$_2$— $^b$ | —CH$_3$ | 101–105° (decomp.) |

$^a$The product is extracted from the aqueous acidic phase with ethyl acetate.
$^b$The acidified aqueous phase is filtered over a strongly acidic ion exchanger (Dowex 50, H$^+$-form) and the product eluted with water.

Example 2

Analogously to Example 1, with the use of R,S-1-aminoethylmethylphosphinic acid, there is obtained R,S-1-phenylacetaminoethylmethylphosphinic acid which is isolated by extraction of the acidified aqueous phase with ethyl acetate and purified by recrystallisation from ethanol; m.p. 173°–175° C.

Example 3

4.3 g. α-Aminobenzylphosphonic acid are heated for 2 hours at 130° C., while stirring, with 11.5 ml. glacial acetic acid and 4.7 g. acetic anhydride. The reaction mixture is evaporated and the residue is dissolved in water, heated for 20 minutes on a waterbath and again evaporated. The syrup which remains behind is dissolved in ethanol with heating and the product precipitated out by the addition of a large amount of diethyl ether. After cooling, it is filtered off with suction. The crude product is recrystallised from ethanol/diethyl ether. There are obtained 4 g. (77% of theory) R,S-α-acetaminobenzylphosphonic acid; m.p. 205°–207° C.

Example 4

2.3 g. R,S-1-amino-2-methylpropylphosphonic acid are dissolved in 30 ml. of water. The pH of the solution is adjusted to 9 by the addition of 4 mol/l sodium hydroxide and 4.5 g. of acetic anhydride thereupon added dropwise. The pH value is maintained at 9 by the addition of 4 mol/l sodium hydroxide. The reaction solution is filtered over 300 ml. of strongly acidic ion exchanger (Dowex 50, H$^+$-form), using water as the elution agent. The product-containing fractions are evaporated and the residue is recrystallised from ethanol/diethyl ether. There is obtained 1.8 g. (73% of theory) R,S-1-acetamino-2-methylpropylphosphonic acid; m.p. 178°–180° C.

Example 5

3.04 g. p-Hydroxyphenylacetic acid and 2.02 g. N-methylmorpholine are dissolved in a mixture of 100 ml. methylene chloride and 10 ml. dimethylformamide. The solution is cooled to −15° C. and mixed dropwise with 2.73 g. isobutyl chloroformate. The reaction mixture is stirred for 30 minutes at 31 15° C. and then a solution of R,S-N-trimethylsilylaminoethylphosphonic acid bis-(trimethylsilyl) ester is added dropwise thereto. The mixture is stirred for 1 hour at −15° C., for 1 hour at 0° C. and for 1 hour at ambient temperature. It is then evaporated to dryness and the residue is taken up in water. The pH value is adjusted to 2 by the addition of some hydrochloric acid, extracted with diethyl ether and subsequently with n-butanol. The butanol phase is evaporated and the residue chromatographed on 1 liter of ion exchanger Dowex 50 in the H$^+$-form with water. The product-containing fractions are evaporated and, for purification, recrystallised from isopropanol/ligroin. There are obtained 38 g. (73% of theory) R,S-1-(p-hydroxyphenylacetamide)-ethylphosphonic acid; m.p. 185°–188° C. (decomp.).

The N-trimethylsilylaminoethylphosphonic acid bis-(trimethylsilyl) ester used as starting material is prepared by heating 3 g. 1-aminoethylphosphonic acid for 15 minutes with 9.4 ml. trimethylchlorosilane and 10.5 ml. triethylamine in 100 ml. methylene chloride. This solution is used directly for the acylation reaction.

Example 6

3.62 g. N-Nitrophenylacetic acid and 2.42 g. N-hydroxysuccinimide were dissolved in a mixture of 20 ml. tetrahydrofuran and 20 ml. methylene chloride and mixed at −10° C. with a solution of 4.54 g. dicyclohexylcarbodiimide in 10 ml. methylene chloride. The reaction mixture is stirred for 1 hour at 0° C. and for 3 hours at ambient temperature. The precipitate obtained is filtered off and digested with hot ethyl acetate. The filtrate is evaporated, the residue is boiled up with ethanol and the solution is cooled.

The product which crystallises out is filtered off with suction. There are obtained 3.75 g. p-nitrophenylacetic acid N-hydroxysuccinimide ester which are dissolved in 50 ml. dimethylformamide and mixed at ambient temperature with a solution of R,S-N-trimethylsilylaminoethylphosphonic acid bis-trimethylsilyl) ester (prepared from 1.88 g. R,S-1-aminoethylphosphonic acid, 5.9 ml. trimethylchlorosilane and 6.55 ml. triethylamine, cf. above). The reaction mixture is stirred for 4 hours at ambient temperature, evaporated and mixed with an aqueous solution of sodium bicarbonate and diethyl ether. The ethereal phase is separated off and the aqueous phase extracted twice with ethyl acetate. Finally, the aqueous phase is acidified with concentrated hydrochloric acid and left in a refrigerator. The precipitated crystals are filtered off with suction and dried. There are obtained 2.1 g (36% of theory) R,S-1-(p-nitrophenylacetamido)-ethylphosphonic acid which, for further purification, can be recrystallised from a mixture of methanol/ethanol and some ligroin; m.p. 210°–215° C. (decomp.).

Example 7

3 g. of the R,S-1-(p-nitrophenylacetamido)-ethylphosphonic acid obtained according to Example 6 are hydrogenated in a mixture of 180 ml. water and 60 ml. ethanol, using palladium/charcoal as catalyst. During the hydrogenation, the product crystallises out. For dissolving the white reaction product, the reaction mixture is mixed with sodium bicarbonate. The catalyst is filtered off and the filtrate adjusted to pH 5 by the addition of 2 mol/l hydrochloric acid. The product which crystallises out after some time is filtered off. There is obtained 1.22 g (45% of theory) R,S-1-(p-aminophenylacetamido)-ethylphosphonic acid, the melting point of which is above 300° C.

2. PREPARATIVE RESOLUTION IN A STIRRER VESSEL REACTOR

Example 8

Resolution of R,S-1-acetaminoethanephosphonic acid 80 g. lyophilised, carrier-bound penicillin G amidase (Boehringer Mannheim GmBH) are vigorously stirred in 1 liter of weakly buffered 0.12 mole/liter substrate solution (TRAP 0.02 mole/liter; pH 7.0) at 37° C. for the period of the reaction, using a paddle stirrer, subsequently filtered off through a suction filter funnel, washed and lyophilised for further use.

FIG. 1 of the accompanying drawings shows the conversion/time diagram of the discontinuous resolution reaction. For the separation of the components, the filtrate is further worked up in known manner (ion exchanger, extraction). In the case of comparatively long reaction time, in order to prevent micro-organism attack, it is recommended to add a preserving agent or to carry out a sterile filtration of the substrate solution.

Example 9

Resolution of R,S-1-phenylacetaminoethanephosphonic acid

This is carried out in a manner analogous to that described in Example 8 but with 500 mg. lyophilised, carrier-bound penicillin G amidase/liter of substrate solution.

FIG. 2 of the accompanying drawings shows the course of the reaction (conversion/time diagram) of the discontinuous resolution reaction.

For working up, one third of the solution of a resolution batch from 250 g. R,S-1-phenylacetaminoethanephosphonic acid (resolution rate 98.2%) is acidified with 150 ml. glacial acetic acid. The mixture is extracted with diethyl ether and the aqueous phase passed over 3 liters of strongly acidic ion exchanger (Dowex 50 in the $H^+$-form). The ion exchanger is eluted with water. The first fraction (2.2 liters) contains acetic acid. In the second fraction (about 2 liters) there is present the S-1-phenylacetaminoethylphosphonic acid. Finally, the R-1-aminoethylphosphonic acid is eluted with about 8 liters of elution volume. The procedure is repeated with the remaining two thirds of the resolution batch. The ninhydrin-positive fractions are combined and evaporated. The crude product obtained is recrtallised from aqueous ethanol. There are obtained 60.1 g. (89% of theory) R-1-aminothylphosphonic acid; m.p. 292°–293° C. (decomp.); $[\alpha]_D^{20} = -15.5°$ (c=2.1 mole/liter NaOH). Optical purity:

(a) from the optical rotation: 96% R enantiomer (literature: $[\alpha]_D^{20} = -16.9°$ (c=2.1 mole/liter NaOH; Antimicr. Ag. Chemother., 15, 677/1979).

(b) gas chromatographically0
  97.5% R enantiomer,
  2.5% S enantiomer.

After trifluoroacetylation with trifluoroacetic anhydride and esterification by heating with triethyl orthoformate, the enantiomers are separated on a chiral phase (Chirasil-Val).

The fractions from the ion exchanger chromatography containing S-1-phenylacetaminoethylphosphonic acid are combined and considerably concentrated. The precipitated crystals are filtered off with suction. There are obtained 58.2 g. (47% of theory) S-1-phenylacetaminoethanephosphonic acid; m.p. 156°–157° C. (content of R enantiomer by gas chromatography investigation: 0.5–1%), The mother liquid is boiled under reflux for 15 hours with concentrated hydrochloric acid. The solution is evaporated and the residue is dissolved in ethanol. Propylene oxide is added dropwise thereto until a pH of 5 to 6 is achieved, then cooled and the precipitated crystals are filtered off with suction. There are obtained 27.4 g. (40% of theory) S-1-aminoethylphosphonic acid; m.p. 284°–285° C. (decomp.); water content 1.3% $[\alpha]_D^{20} = +15°$ (c=2.1 mole/liter NaOH).

Optical purity:
(a) from the optical rotation: 95% S-enantiomer (literature: $[\alpha]_D^{20} = +16.8°$ (c=2.1 mole/liter NaOH; Antimicr. Ag. Chemother., 15, 377/1979).

(b) gas chromatographically:
  96–97% S-enantiomer,
  3–4% R enantiomer.

(In this case, the trifluoroacetylation is carried out with N-methyl-bis-trifluoroacetamide).

In the following Table 2, there are summarised the resolution rate for various R,S-1-acylaminoalkylphosphonic acids obtained analogously to Examples 8 and 9:

TABLE 2

| substrate | immob. Pen-G-amidase (U/g.) | resolution rate % R | | | |
|---|---|---|---|---|---|
| | | 1 h. | 24 h. | 48 h. | 76 h. |
| Ph—O—CH₂—C(O)—NH—CH(CH₃)—P(O)(OH)₂  R,S | 94 | 32 | 45 | 46 | 45 |
| Ph—CH₂—CO—NH—CH(CH(CH₃)₂)—P(O)(OH)₂  R,S | 0.4 | 2 | 12 | 18 | 32 |
| Ph—CH₂—C(O)—NH—CH(CH₂CH(CH₃)₂)—P(O)(OH)₂  R,S | 6.3 | 6 | 19 | 28 | 45 |
| Ph—CH₂—C(O)—NH—CH(CH₂Ph)—P(O)(OH)₂  R,S | 2.8 | 4 | 15 | 25 | 38 |
| Ph—CH₂—C(O)—NH—CH(Ph)—P(O)(OH)₂  R,S | 44 | 30 | 48 | 42 | 45 |
| Ph—CH₂—C(O)—NH—CH(CH₂OH)—P(O)(OH)₂  R,S | 1055 | 46 | 49 | 44 | 45 |
| Ph—CH₂—C(O)—NH—CH(CH₃)—P(O)(OH)₂  R,S | 1110 | 45 | 42 | 45 | 46 |
| CH₃O—C₆H₄—CH₂—CO—NH—CH(CH₃)—P(O)(OH)₂  R,S | 565 | 42 | 45 | 45 | 46 |
| HO—C₆H₄—CH₂—CO—NH—CH(CH₃)—P(O)(OH)₂  R,S | 710 | 40 | 48 | 47 | 48 |

TABLE 2-continued

| substrate | immob. Pen-G-amidase (U/g.) | resolution rate % R | | | |
|---|---|---|---|---|---|
| | | 1 h. | 24 h. | 48 h. | 76 h. |
| 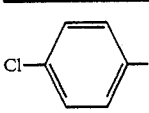 Cl—⟨C6H4⟩—CH2—CO—NH—CH(CH3)—P(O)(OH)2  R,S | 620 | 35 | 46 | 40 | 45 |
| 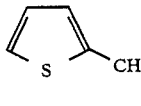 ⟨thienyl-S⟩—CH2—CO—NH—CH(CH3)—P(O)(OH)2  R,S | 760 | 39 | 44 | 45 | 43 |
| CH3—(CH2)4—CONH—CH(CH3)—P(O)(OH)2  R,S | 62 | 21 | 38 | 43 | 42 |
| 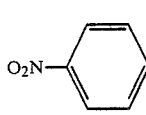 O2N—⟨C6H4⟩—CH2—CONH—CH(CH3)—P(O)(OH)2  R,S | 24 | 12 | 28 | 32 | 36 |
| 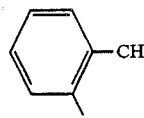 ⟨o-tolyl⟩—CH2—CONH—CH(CH3)—P(O)(OH)2  R,S | 74 | 19 | 35 | 44 | 42 |

We claim:

1. A process for the preparation of the stereoisomers substituted or unsubstituted of 1-aminoalkylphosphonic acids and of 1-aminoalkylphosphinic acids comprising resolving by enzymatically splitting of their racemic N-acyl derivatives with penicillin G amidase, subsequently deacylating the resolved derivatives, and recovering the stereoisomer.

2. The process of claim 1, wherein penicillin G amidase from *Escherichia coli* is used.

3. The process of claim 1, wherein penicillin G amidase from *Escherichia coli*, DSM 1900 (ATCC 11105) is used.

4. The process of claim 1, wherein the penicillin G amidase is used in immobilised form.

5. The process of claim 4, wherein the enzymatic splitting is carried out in a stirred vessel or in a column reactor.

6. The process of claim 5, wherein the enzymatic splitting is carried out a temperature of from 20° to 60° C.

7. The process of claim 6, wherein the enzymatic splitting is carried out at a temperature of 37° C.

8. The process of claim 6, wherein the enzymatic splitting is carried out at a pH value of from 5.5 to 8.5.

9. The process of claim 8, wherein the enzymatic splitting is carried out at a pH of 7.

10. The process of claim 1 wherein the enzymatic splitting is carried out at a temperature from 20° to 60° C. and a pH value from 5.5 to 8.5.

11. The process of claim 10 wherein the enzymatic splitting is carried out at a temperature of 37° C.

12. The process of claim 11 wherein the enzymatic splitting is carried out at a pH of 7.

* * * * *

UNITED STATES PATENT AND TRADEMARK OFFICE
CERTIFICATE OF CORRECTION

PATENT NO.  : 4,859,602
DATED       : August 22, 1989
INVENTOR(S) : Gerd Zimmermann et al.

It is certified that error appears in the above-identified patent and that said Letters Patent is hereby corrected as shown below:

Col. 1, lines 9 & 11:   change "1-aminoalkylphosphonic" to
                        -- 1-aminoalkylphosphinic --.

Col. 3, line 66:        change "acylaminoalkylphosponic"
                        to -- acylaminoalkylphosphonic --.

Col. 4, line 2:         change "S-1-acylaminoalkylphosphinic"
                        to -- S-1-acylaminoalkylphosphonic --.

Col. 4, line 46:        change "hydroxy" to -- hydroxyl --.

Col. 8, line 43:        change "30 minutes at 31 15°C" to
                        -- 30 minutes at -15°C --.

Signed and Sealed this

Sixteenth Day of October, 1990

Attest:

HARRY F. MANBECK, JR.

*Attesting Officer*          *Commissioner of Patents and Trademarks*